United States Patent
Hatanaka et al.

(10) Patent No.: US 9,364,142 B2
(45) Date of Patent: Jun. 14, 2016

(54) SIMULATION DEVICE, SIMULATION SYSTEM, SIMULATION METHOD AND SIMULATION PROGRAM

(71) Applicant: HOYA CORPORATION, Tokyo (JP)

(72) Inventors: Takashi Hatanaka, Tokyo (JP); Hua Qi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 14/416,246

(22) PCT Filed: May 28, 2013

(86) PCT No.: PCT/JP2013/064707
§ 371 (c)(1),
(2) Date: Mar. 25, 2015

(87) PCT Pub. No.: WO2014/030403
PCT Pub. Date: Feb. 27, 2014

(65) Prior Publication Data
US 2015/0238076 A1 Aug. 27, 2015

(30) Foreign Application Priority Data
Aug. 20, 2012 (JP) .................................. 2012-181639

(51) Int. Cl.
 A61B 3/10 (2006.01)
 A61B 3/04 (2006.01)
 A61B 3/00 (2006.01)
 G02C 7/02 (2006.01)
(52) U.S. Cl.
 CPC ................ *A61B 3/04* (2013.01); *A61B 3/0041* (2013.01); *G02C 7/028* (2013.01)
(58) Field of Classification Search
 CPC ....................... A61B 2019/524; A61B 2576/00
 USPC ................ 351/246, 211, 221; 703/11, 21, 22; 382/107
 See application file for complete search history.

(56) References Cited

U.S. PATENT DOCUMENTS

2004/0257527 A1 12/2004 Qi et al.
2005/0089194 A1* 4/2005 Bell ...................... G06F 3/0425
382/103

(Continued)

FOREIGN PATENT DOCUMENTS

EP 0734683 A2 10/1996
EP 1 158 338 A2 11/2001

(Continued)

OTHER PUBLICATIONS

Jul. 2, 2013 International Search Report issued in International Application No. PCT/JP2013/064707.

(Continued)

*Primary Examiner* — Hung Dang
(74) *Attorney, Agent, or Firm* — Oliff PLC

(57) ABSTRACT

There is provided a simulation device including: first blur component generating unit configured to generate a first blur component based on distance data included in observation scene data in which the distance data is added to a computer graphics image, and a parameter regarding the non-progressive component included in the trial lens; second blur component generating unit configured to generate a second blur component based on distance data included in the observation scene data and a parameter regarding a progressive component included in the progressive addition lens; a display blur component generating unit configured to generate display blur component, based on first blur component and second blur component; a display blur component adding unit configured to add display blur component to the observation scene data; and display unit configured to display an observation image obtained by display blur component adding unit, to a wearer wearing the trial lens.

9 Claims, 8 Drawing Sheets

(56) References Cited

U.S. PATENT DOCUMENTS

2008/0316427 A1* 12/2008 Fisher ............... G06F 17/5009
 351/233
2010/0179799 A1 7/2010 Shinohara et al.

FOREIGN PATENT DOCUMENTS

| JP | 2005-308490 A | 11/2005 |
|---|---|---|
| JP | 4124468 B2 | 7/2008 |
| JP | 4477909 B2 | 6/2010 |
| JP | 2010-165045 A | 7/2010 |
| JP | 2012-066002 A | 4/2012 |
| WO | 2007056795 A1 | 5/2007 |

OTHER PUBLICATIONS

Apr. 29, 2016 Extended European Search Report issued in Application No. 13830333.4.

* cited by examiner

31 FIRST BLUR COMPONENT GENERATING UNIT
31' FIRST DISTORTION COMPONENT GENERATING UNIT
4 DISPLAY BLUR COMPONENT GENERATING UNIT
4' DISPLAY DISTORTION COMPONENT GENERATING UNIT
32 SECOND BLUR COMPONENT GENERATING UNIT
32' SECOND DISTORTION COMPONENT GENERATING UNIT

SIMULATION DEVICE, SIMULATION SYSTEM, SIMULATION METHOD AND SIMULATION PROGRAM

TECHNICAL FIELD

The present invention relates to a simulation device, a simulation system, a simulation method and a simulation program, and particularly to the simulation device, system, method and program using a trial lens.

DESCRIPTION OF RELATED ART

Currently, various types of spectacle lenses are developed according to desires of wearers, such as a lens responding to myopia, hyperopia, or astigmatism. Thus, an appropriate spectacle lens suited to the desires of the wearers can be provided. To provide such an appropriate spectacle lens to each wearer, it is necessary that the wearer has an experience of a view when wearing the spectacle lens as a product. Originally, it is preferable that the wearer has a view by previously preparing the spectacle lens as a product. However, the spectacle lens as a product is a custom-made product which is made so as to suit to each wearer, and it is impossible to make the spectacle lens every time the wearer has an experience of a view.

The following method is frequently used for testing whether or not power of the spectacle lens is appropriate: that is, a trial lens (test lens) is attached to a test frame (spectacle test frame, or trial frame), then a user wears the test frame with a trial lens. Typically, the trial lens has three types such as a lens for spherical power, a lens for cylindrical power, and a lens for prismatic power. In the case of a single vision lens, the three kinds of lenses are used in combination. In the case of a prescription for progressive addition lens, a plano trial lens is further added (for example, see patent document 1 by the present applicant). The test frame has attachment positions so that three or four trial lenses can be attached, and when a plurality of trial lenses are attached, a trial lens of a weak power is attached to outside (object side), and a trial lens of a strong power is attached to inside (eye side). These trial lenses are test lenses corresponding to a prescription power for a distance vision. Then, a progressive trial lens provided from each spectacle lens maker is further superposed thereon, and is attached to the test frame.

Meanwhile, there is also a method of not using the trial lens or the test frame (for example, see patent document 2). Patent document 2 teaches as follows: when a patient (wearer in this specification) already wears a spectacle (spectacle optical system), and when the wearer views an outer visual field through a virtual lens (spectacle lens as a final product), the wearer percepts an image with a distortion fused therein, which is caused by the spectacle optical system worn by the wearer him/herself, as a simulation image (paragraph [0005] of patent document 2). Then, such a simulation image is subjected to image processing so as to cancel the distortion generated by the spectacle optical system worn by the wears themselves (paragraph [0009] in patent document 2).

PRIOR ART DOCUMENT

Patent Document

Patent document 1: Patent publication No. 4124468
Patent document 2: Patent publication No. 4477909

SUMMARY OF THE INVENTION

Problem to be Solved by the Invention

According to the method of patent document 1, a plurality of trial lenses are attached to the test frame. In other words, a view through a plurality of lenses is used as a result. However, after examination by inventors of the present invention, it is found that the view through a plurality of lenses and a view through one spectacle lens are significantly different from each other. In addition, when the finished spectacle lens provided to the wearer is a progressive addition lens, the above difference is generated remarkably. Further, when the progressive addition lens is provided one by one for right and left eyes respectively, the wearer further percepts the difference between the view when using the trial lenses, and a view when wearing an actual spectacle lens.

The method described in patent document 2 is the method for canceling the distortion caused by the spectacle optical system worn by a wearer himself/herself, and is not based on a concept that the trial lens is used. Further, the method described in patent document 2 is the method requiring the spectacle optical system worn by the wearer himself/herself. This is because when the method described in patent document 2 is applied to the wearer, the wearer cannot experience a simulation result unless the wearer views through his/her own spectacle. However, the optical shop cannot perform on-site simulation without optical data of the spectacle optical system worn by the wearer. In that case the optical data of the wearer needs to be generated newly.

In this viewpoint, the method of using the trial lens and the test frame is considered as a useful choice of having an experience of a view, because the result of the experience of a view can be provided to the wearer without depending on the spectacle lens worn by the wearer him/herself.

Nevertheless, as described above, in the case of the progressive addition lens based on an individual design, which is a lens of a type designed so as to suit a spectacle wearing condition or a lifestyle of an individual wearer, the lens is designed according to each individual wearer. Therefore, the trial lens for confirming the view is not prepared as one lens completely matching each individual wearer. Thus, when trying to handle with one lens completely matched to the wearer, extremely many kinds of trial lenses must be prepared, and this is not practical.

Further, in a conventional device using the trial lens, a plurality of trial lenses must be used, and as described above, a significant difference is generated between the view through a plurality of lenses and the view through one finished spectacle lens.

Therefore, an object of the present invention is to provide a simulation device, a system, a method, and a program capable of reducing a difference between the view when having the experience of a view through trial lenses, and the view when actually wearing a progressive addition lens.

Means for Solving the Problem

In order to solve the above-described problem, inventors of the present invention consider the difference between the view when wearing a plurality of trial lenses, and the view when actually wearing the progressive addition lens. As a result, it is so judged that the difference between them is divided into the difference of "blur" and the difference of "distortion". Patent document 2 focuses on the difference of "distortion" only, and teaches a method of canceling the difference of "distortion", but does not refer to the difference of "blur".

The "blur" is generated because an object viewed by the wearer is not precisely focused. That is, when viewing a predetermined distance away object, the object is not precisely focused when wearing one finished progressive addition lens, even if precise focusing is achieved when wearing a plurality of trial lenses. That is, it is found by the inventors of the present invention, that the difference of a view is mainly caused by the "blur", and the "blur" is caused by a plurality of trial lenses.

However, as described above, preparing one trial lens means that the finished progressive addition lens is manufactured and provided to the wearer finally. It is not practical to manufacture the finished progressive addition lens to be provided to the wearer, every time the test wearing is performed. Even if the simulation is performed using optical data like a virtual lens of patent document 2 without actually manufacturing the finished progressive addition lens to be provided to the wearer, it is necessary to cancel the distortion of an observation system, and therefore an observer must previously obtain missing optical data regarding the spectacle worn by the wearer himself/herself. Therefore, there is a large hurdle to practical use. Even if the practical use is realized, it is only the "distortion" that can be reproduced, and the "blur" cannot be reproduced.

Under such a circumstance, the inventors of the present invention further study on the technique of having an experience of a view using the trial lens. As a result, the inventors of the present invention achieve a technique of making the trial lens share the role for a view corresponding to a non-progressive component, and making an observation image share the role for a view corresponding to a progressive component, that is, a breakthrough technique of a role-sharing is achieved by the inventors of the present invention, so that an object (trial lens) shares the role for the view corresponding to the non-progressive component, and the image shares the role for the view corresponding to the progressive component.

However, in this state, since the simulation is performed while wearing the trial lens by the wearer, the wearer views the observation image added with blur corresponding to the progressive component under influence of the blur caused by the trial lens. Then, a doubled blurring situation is displayed for the wearer as a result of the simulation. Therefore, as a result of further strenuous technical efforts by the inventors of the present invention, an unconventional concept is achieved as follows: in addition to the role-sharing for the view as described above, the observation image that shares the role for the view corresponding to the progressive component, is the image from which blur caused by the trial lens (non-progressive addition lens) is removed from observation scene data which is a pre-stage of the observation image.

Patent document 2 neither discloses nor suggests the role-sharing for the view as described above, such that the object (trial lens) shares the role for the view corresponding to the non-progressive component, and the image shares the role for the view corresponding to the progressive component.

Further, patent document 2 teaches that blur is generated in a virtual lens (finished spectacle lens provided to the wearer) (for example see paragraph [0051] of patent document 2). However, patent document 2 does not teach a point that the simulation result is influenced by the blur caused by the spectacle optical system. There is no description in patent document 2 such that the trial lens is used as the spectacle optical system, and there is no description regarding the image processing performed to remove the blur in the spectacle optical system.

Based on the above-described knowledge, the present invention has the following aspects.

According to a first aspect of the present invention, there is provided a simulation device for having an experience of a view by a wearer when an outer visual field is observed through a progressive addition lens, by observing an observation image through a set of trial lenses, wherein a trial lens is a non-progressive addition lens having a non-progressive component of the progressive addition lens, and shares a role for a view corresponding to a non-progressive component of the progressive addition lens, and the observation image shares a role for a view corresponding to a progressive component of the progressive addition lens, the simulation device including:

a first blur component generating unit configured to generate a first blur component based on distance data included in observation scene data in which the distance data is added to a computer graphics image, and a parameter regarding the non-progressive component included in the trial lens;

a second blur component generating unit configured to generate a second blur component based on distance data included in the observation scene data and a parameter regarding a progressive component included in the progressive addition lens;

a display blur component generating unit configured to generate a display blur component, based on the first blur component and the second blur component;

a display blur component adding unit configured to add the display blur component to the observation scene data; and a display unit configured to display an observation image obtained by the display blur component adding unit, to a wearer wearing the trial lens.

According to a second aspect of the present invention, there is provided the simulation device of the first aspect, wherein the display blur component is the component in which the first blur component is removed from the second blur component.

According to a third aspect of the present invention, there is provided the simulation device of the second aspect, further including:

a first distortion component generating unit configured to generate a first distortion component based on the distance data included in the observation scene data and a parameter regarding a non-progressive component included in the trial lens;

a second distortion component generating unit configured to generate a second distortion component, based on distance data included in the observation scene data and a parameter regarding a progressive component included in the progressive addition lens;

a display distortion component generating unit configured to generate a display distortion component, based on the first distortion component and the second distortion component; and a display distortion component adding unit configured to add the display distortion component to the observation scene data, wherein an observation image obtained by the display distortion component adding unit, is displayed by the display unit, to a wearer wearing the trial lens.

According to a fourth aspect of the present invention, there is provided the simulation device of the third aspect, wherein at least the display blur component adding unit and the display distortion component adding unit respond to each of a left eye and a right eye individually.

According to a fifth aspect of the present invention, there is provided the simulation device of the fourth aspect, wherein the display unit is assembled into a casing that can be mounted on a head section of a wearer.

According to a sixth aspect of the present invention, there is provided the simulation device of the fifth aspect, including a third blur component generating unit configured to generate a third blur component, based on distance information between the observation image displayed in the casing and a wearer wherein in the display blur component adding unit, the third blur component generated by the third blur component generating unit is removed from the observation scene data.

According to a seventh aspect of the present invention, there is provided a simulation system for having an experience of a view by a wearer when an outer visual field is observed through a progressive addition lens, by observing an observation image through a trial lens, wherein the trial lens is a non-progressive addition lens having a non-progressive component of the progressive addition lens, and shares a role for a view corresponding to a non-progressive component of the progressive addition lens, and the observation image shares a role for a view corresponding to a progressive component of the progressive addition lens, the simulation system including:

a first blur component generating unit configured to generate a first blur component based on distance data included in observation scene data in which the distance data is added to a computer graphics image, and a parameter regarding the non-progressive component included in the trial lens;

a second blur component generating unit configured to generate a second blur component based on the distance data included in the observation scene data and a parameter regarding a progressive component included in the progressive addition lens;

a display blur component generating unit configured to generate a display blur component, based on the first blur component and the second blur component;

a display blur component adding unit configured to add the display blur component to the observation scene data; and a display unit configured to display an observation image obtained by the display blur component adding unit, to a wearer wearing the trial lens.

According to an eighth aspect of the present invention, there is provided a simulation method for having an experience of a view by a wearer when an outer visual field is observed through a progressive addition lens, by observing an observation image through a trial lens, wherein the trial lens is a non-progressive addition lens having a non-progressive component of the progressive addition lens and shares a role for a view corresponding to a non-progressive component of the progressive addition lens, and the observation image shares a role for a view corresponding to a progressive component of the progressive addition lens, the simulation method including:

generating a first blur component based on distance data included in observation scene data in which the distance data is added to a computer graphics image, and a parameter regarding the non-progressive component included in the trial lens;

generating a second blur component based on distance data included in the observation scene data and a parameter regarding a progressive component included in the progressive addition lens;

generating a display blur component, based on the first blur component and the second blur component;

adding the display blur component to the observation scene data; and displaying an observation image obtained by the display blur component generating unit and the display blur component adding unit, to a wearer wearing the trial lens.

According to a ninth aspect of the present invention, there is provided a simulation program for having an experience of a view by a wearer when an outer visual field is observed through a progressive addition lens, by observing an observation image through a trial lens, wherein the trial lens is a non-progressive addition lens having a non-progressive component of the progressive addition lens and shares a role for a view corresponding to a non-progressive component of the progressive addition lens, and the observation image shares a role for a view corresponding to a progressive component of the progressive addition lens, the simulation program configured to cause a computer to function as:

a first blur component generating unit configured to generate a first blur component based on distance data included in observation scene data in which the distance data is added to a computer graphics image, and a parameter regarding the non-progressive component included in the trial lens;

a second blur component generating unit configured to generate a second blur component based on distance data included in the observation scene data and a parameter regarding a progressive component included in the progressive addition lens;

a display blur component generating unit configured to generate a display blur component, based on the first blur component and the second blur component;

a display blur component adding unit configured to add the display blur component to the observation scene data; and a display unit configured to display an observation image obtained by the display blur component adding unit, to a wearer wearing the trial lens.

Advantage of the Invention

According to the present invention, the difference between the view when having the experience of a view using the trial lens and the view when actually wearing the progressive addition lens, can be reduced.

DETAILED DESCRIPTION OF THE INVENTION

Figure 1:
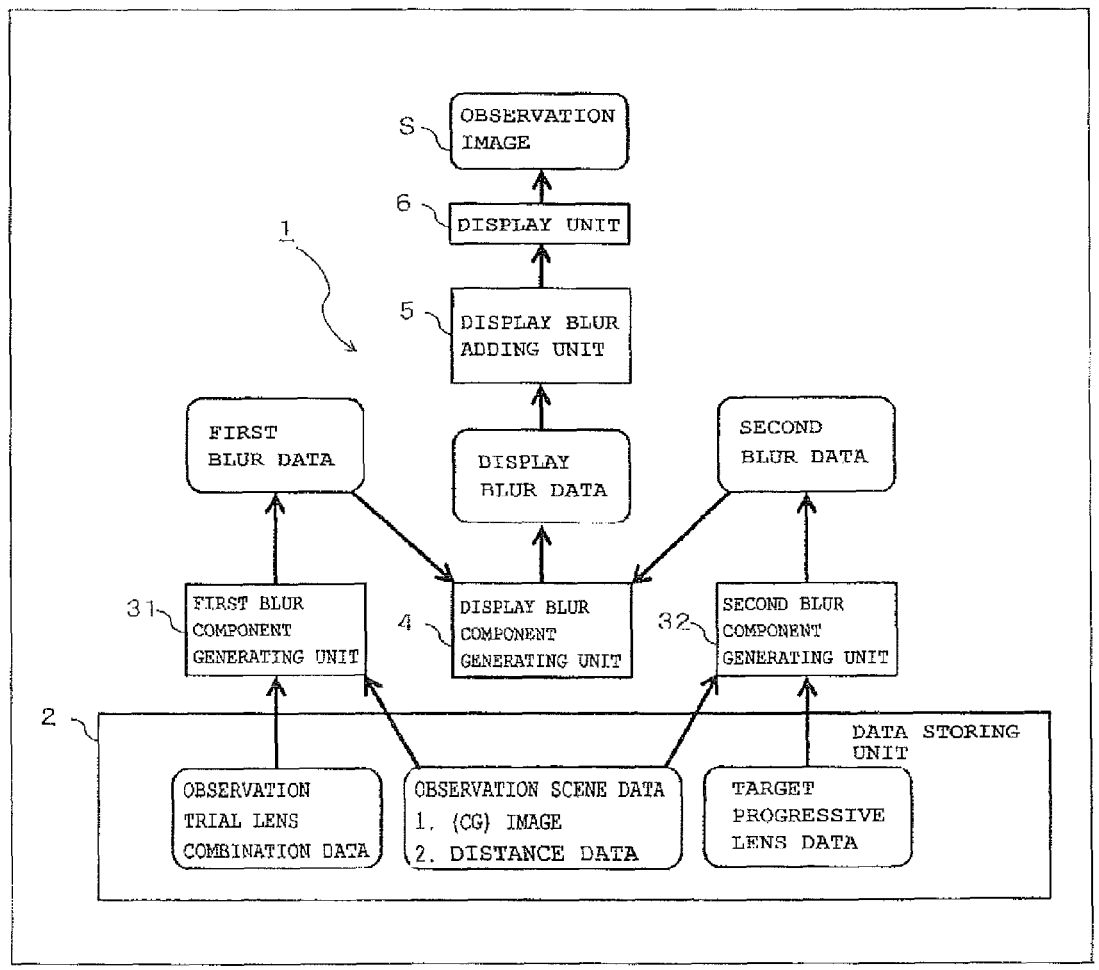
FIG. 1 is a block diagram showing an example of a function configuration of a simulation device according to an embodiment of the present invention.

Embodiments of the present invention will be described hereafter. In [Embodiment 1], explanation is given in the following order.
1. Schematic structure of a simulation device
2. Function configuration of a simulation device
3. Procedure of a simulation device
4. Effect of this embodiment Note that in [Embodiment 2], an embodiment of removing and adding not only a blur component but also a distortion component, will be described. Specifically, the following content will be described.
1. Means regarding the distortion component
2. Procedure of the simulation processing regarding the distortion component Further, in [Embodiment 3], the structure of the simulation device of [Embodiment 1] is formed into a network and formed into a program, and such a network system (simulation system) and the program will be described.

Further, in [Embodiment 4], other modified example will be described.

Embodiment 1

<Schematic Structure of a Simulation Device 1>

First, a schematic structure of a simulation device 1 according to this embodiment will be described.

FIG. 1 is a block diagram showing an example of a function configuration of the simulation device 1 according to this embodiment.

The structure of the simulation device 1 according to this embodiment has a structure in which the following each unit is provided in a control computer unit.

"Data storing unit 2" configured to store observation scene data including distance data, and a parameter regarding a progressive addition lens to be simulated.

"First blur component generating unit 31" configured to retrieve data regarding image information, distance data, and non-progressive component from the data storing unit 2, and generating a first blur component due to the non-progressive component shared by the trial lens, out of optical parameters of the progressive addition lens to be simulated.

"Second blur component generating unit 32" configured to retrieve data regarding image information, distance data, and progressive component from data storing unit 2, and generating a second blur component due to the progressive component shared by an observation image S, out of optical parameters of the progressive addition lens to be simulated.

"Display blur component generating unit 4" configured to generate a display blur component, from the first blur component (first blur data) and the second blur component (second blur data).

"Display blur component adding unit 5" configured to add the display blur component (display blur data) of the display blur component generating unit 4, to observation scene data.

"Display unit 6" configured to display the observation image S after adding the display blur data to the observation scene data.

Figure 2:
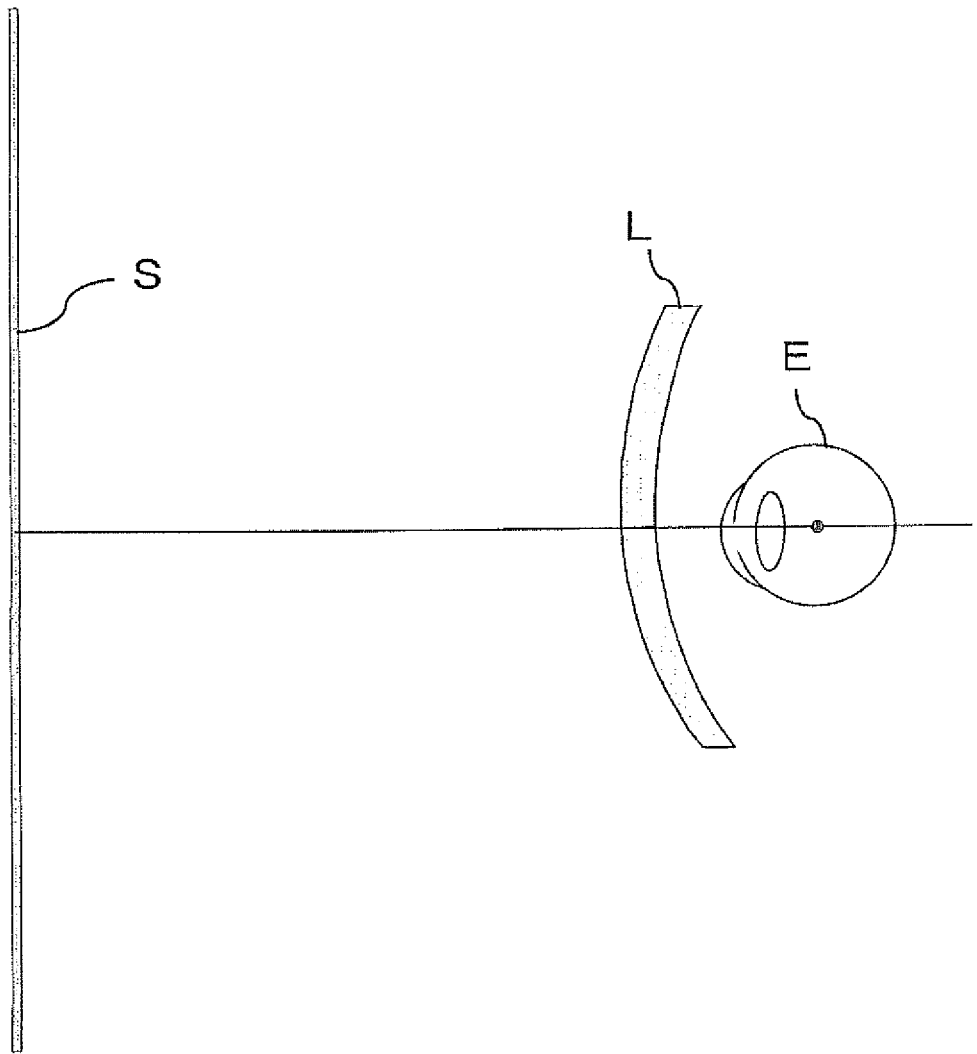
FIG. 2 is a cross-sectional schematic view showing a simulation state according to an embodiment of the present invention.

Then, as shown in FIG. 2, by observing the observation image S displayed by the display unit 6 by a user (wearer) wearing a trial lens L, the experience of a view when observing the outer visual field through the progressive addition lens, can be provided to the wearer. Note that symbol E in FIG. 2 indicates an eyeball of the wearer.

<2. Function Configuration of the Simulation Device 1>
(Control Computer Unit)

A control computer unit has a function as a computer device that performs information processing indicated by a specific program, and specifically, is constituted of a combination of CPU (Central Processing Unit), HDD (Hard disk drive), ROM (Read Only Memory), RAM (Random Access Memory), and external interface (I/F), etc. The control computer unit is a central portion that functions as each of the aforementioned units, in the simulation device 1 of this embodiment.

(Data Storing Unit 2)

The data storing unit 2 has a function of storing data required for giving an experience of a view to the wearer when observing the outer visual field through the progressive addition lens. HDD given above, and a server, etc., in a network can be given for example, as the data storing unit 2. Further, mainly the following three kinds of data can be given as the data stored in the data storing unit 2.

First data is the observation scene data which is a base of the observation image S finally displayed for the wearer. The observation scene data is the data in which distance data is added to a computer graphics image (CG image) reflecting an observation image such as a landscape or an object. The distance data may be added in each pixel of the CG image.

Second data is the data regarding the trial lens L used for simulation (observation trial lens combination data).

Data regarding the trial lens L is the data mainly regarding the non-progressive component, and is the data regarding spherical power (prescription power for distance vision), astigmatic power and its astigmatic axis, prism power and its base direction, etc., for example, other than the progressive component. These data can be acquired by optometry before simulation.

Third data is the data regarding the progressive addition lens to be simulated (progressive lens data to be simulated).

The data regarding the progressive addition lens is the data mainly regarding the progressive component, and the data showing components regarding progression, such as an addition power and a power distribution, etc., can be given for example. In this case, in order to obtain the data regarding the progressive component and specialized for the progressive component, for example various kinds of data having different addition powers are prepared while having a fixed distance power. Of course, the other data (such as spherical power) may be further included in the progressive addition lens to be simulated.

The "data regarding the progressive addition lens" and the "data regarding the trial lens L" are collectively called "data regarding a lens (lens data)" hereafter.

(First Blur Component Generating Unit 31)

A first blur component generating unit 31 retrieves the observation scene data and the data regarding the trial lens L from the data storing unit 2, and has a function of generating the first blur component based on the distance data included in the observation scene data and the parameter regarding the non-progressive component included in the trial lens L. The first blur component is caused by the non-progressive component shared by the trial lens L, and converted to first blur data.

(Second Blur Component Generating Unit 32)

A second blur component generating unit 32 retrieves the observation scene data and the data regarding the progressive addition lens to be simulated from the data storing unit 2, and has a function of generating the second blur component based on the distance data included in the observation scene data and the parameter regarding the progressive component included in the progressive addition lens. The second blur component is generated due to the progressive component shared by the image, and converted to second blur data.

(Display Blur Component Generating Unit 4)

A display blur component generating unit 4 retrieves first blur data from the first blur component generating unit 31, and retrieves second blur data from the second blur component generating unit 32, and has a function of generating the display blur component based on the first blur data and the second blur data.

The display blur component is the component influenced by both of the non-progressive component shared by the trial lens L and the progressive component shared by the image, and converted to display blur data. Wherein, the CG image is influenced by the blur due to the progressive component included in the progressive addition lens. Simultaneously, the blur caused by the trial lens L is removed from the CG image. A removing method and an adding method are specifically described in detail in <3. Procedure of simulation processing>

(Display Blur Component Generating Unit 5)

A display blur component generating unit 5 retrieves display blur data from the display blur component generating unit 4, and has a function of adding the display blur data to the CG image.

(Display Unit 6)

A display unit 6 has a function of displaying the observation image S obtained by the display blur component adding unit 5, to the wearer wearing the trial lens L. The display unit 6 may be a publicly-known unit such as a general displayer or a printed image, etc. However, if a suitable example is given, the display unit 6 is preferably a head mounted display (abbreviated as "HMD unit" hereafter). An example of using the HMD unit as the display unit 6, will be described hereafter.

An image displayer is disposed in front of an eye of the wearer when wearing the casing of the HMD unit. The image displayer displays an image to the wearer. Use of the image displayer configured by utilizing LCD (Liquid Crystal Display) can be considered. As described in detail later, a simulation image which is the image supposed to be viewed through the progressive addition lens by the wearer, is given as the image displayed and outputted by the image displayer. The image displayer is preferably constituted of panels individually responding to a simulation image for a left eye and a simulation image for a right eye respectively, that is, a left eye display panel and a right eye display panel. Further, the image displayer preferably responds to display and output of a moving image. The image displayer is simply called a screen hereafter.

The control computer unit may be assembled into the casing of the HMD unit or may be provided separately from the HMD unit. When it is provided separately from the HMD unit, the control computer unit is capable of carrying out communication with the HMD unit via wire or wireless communication line.

<3. Procedure of Simulation Processing>

In the simulation device 1 configured as described above, an execution procedure of the simulation processing performed for having a virtual experience of a wearing state of the progressive addition lens, will be described next.

Figure 3:
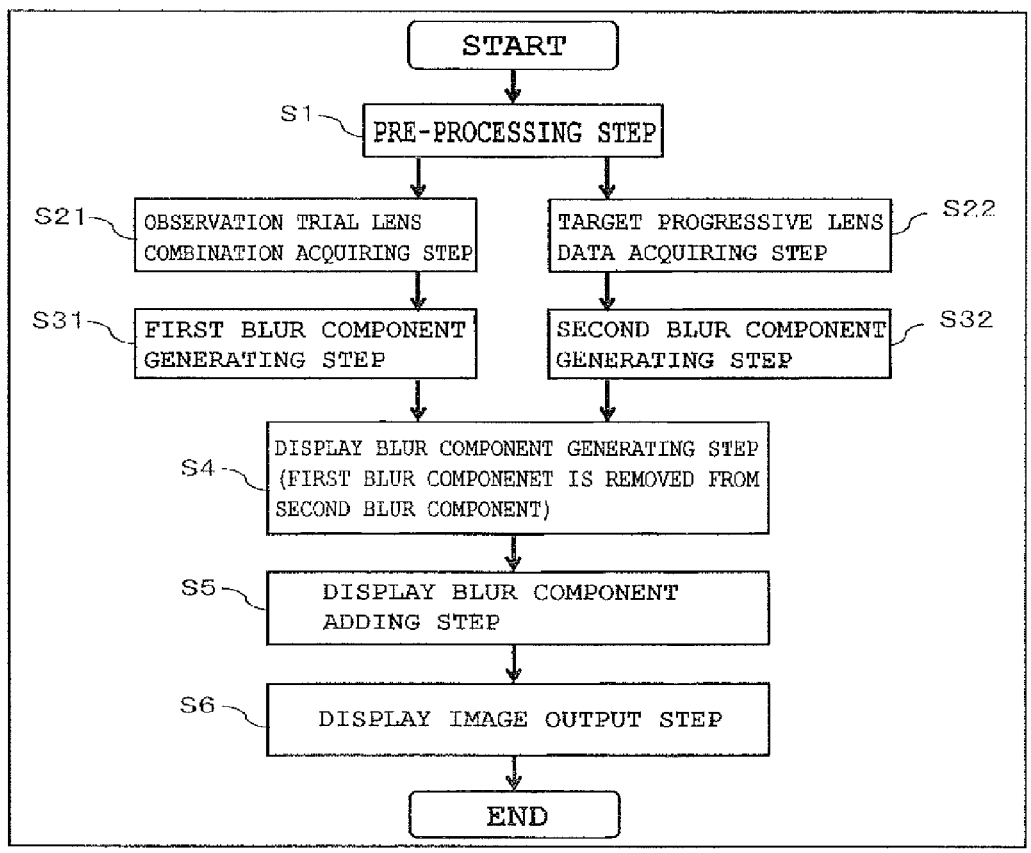
FIG. 3 is a flowchart showing an example of an execution procedure of a simulation processing performed by the simulation device according to an embodiment of the present invention.

FIG. 3 is a flowchart showing an example of the execution procedure of the simulation processing performed by the simulation device 1 of this embodiment.

An outline of the simulation processing described in this embodiment is as follows.

First, the simulation processing is divided into two routes starting from a pre-processing step (S1). The two routes are a route (S21 to S31) for generating the first blur component shared by the trial lens L (non-progressive component), and a route (S22 to S32) for generating the second blur component due to the progressive component shared by the image. These two routes are merged finally, and processing is advanced to a display blur component adding step (S5) of adding a display blur component to the CG image, and a display image output step (S6) of displaying the observation image S on the display unit 6 after processing the CG image.

(S1 Pre-Processing Step)

In the pre-processing step (S1), lens data regarding the progressive addition lens scheduled to be worn by the wearer, and further lens data regarding the trial lens L are prepared, prior to a series of processing thereafter. More specifically, the lens data is stored in the data storing unit 2, and which lens data is used, is determined as the data causing the first blur component generated by the first blur component generating unit 31, and the second blur component generated by the second blur component generating unit 32. Further, the kind or the number of the trial lens L is also determined.

Note that, the progressive addition lens or the trial lens L to be worn by the wearer, may be specified by a clerk of a spectacle shop while following an operation content of an operating unit not shown of the HMD unit or the control computer unit.

(S21 Observation Trial Lens Combination Acquiring Step)

In an observation trial lens combination acquiring step (S21), the non-progressive component caused by the trial lens L (non-progressive lens) is acquired from the data storing unit 2 by the first blur component generating unit 31. In this case, the first blur component generating unit 31 also acquires the observation scene data from the data storing unit 2.

(S31 First Blur Component Generating Step)

In a first blur component generating step (S31), a generation mode of the blur of the image generated when viewing the outer visual field through a specific kind and number of trial lens L by the wearer, is specified by the first blur component generating unit 31. The reason for generating the blur in the image when viewing an object through the trial lens L is that all visual rays from an object point does not converge on one point of retina. That is, rays from an object point form a light distribution that spreads extending in a certain range with an image point as a center.

Such a distribution is called a Point Spread Function (abbreviated as "PSF" hereafter). Accordingly, the generation mode of the blue of the image can be specified by obtaining PSF.

However, even if the object is viewed through the same position on the trial lens L, PSF is different if the distance of the object points is different. Meanwhile, in the first blur component generating unit 31, the distance of constituent elements (for example, each of pixels) of an original image is found by the distance data acquired by the observation trial lens combination acquiring step (S21), and therefore PSF which is different depending on the distance, can be properly obtained. PSF is obtained as follows: an arbitrary light transmission point in the trial lens L is recognized based on the lens data acquired by the pre-processing step (S1), and a value of the distance of the observation objects is recognized based on a depth image acquired by the observation trial lens combination acquiring step (S21), and thereafter PSF is obtained using a publicly-known technique such as ray tracing (see Specification of U.S. Pat. No. 3,342,423, International Publication No. 2010/044383, etc.).

(S22 Target Progressive Lens Data Acquiring Step)

In a target progressive lens data acquiring step (S22), the progressive component of the progressive addition lens to be simulated, is acquired from the data storing unit 2 by the second blur component generating unit 32. In this case, the second blur component generating unit 32 also acquires the observation scene data from the data storing unit 2.

(S32 Second Blur Component Generating Step)

In the second blur component generating step (S32), the second blur component is generated. As a specific technique, the technique similar to the technique of the first blur component generating step (S31) may be used. That is, PSF is obtained based on the data regarding the progressive addition lens.

(S4 Display Blur Component Generating Step)

Here, the display blur component is generated in consideration of both of the first blur component and the second blur component. In this embodiment, unlike a conventional technique, the blur caused by the trial lens L must be removed from the finally generated observation image S.

The display blur component (display blur data) is generated as follows for example.

First, the luminance of each pixel is distributed to the peripheral pixels based on the PSF, and can be reflected by reconstructing the luminance of all pixels in the image. Such a process is also referred to as a convolution calculation (Convolution).

The above operation is called a PSF convolution the case of viewing a screen along the PSF of the image and a ray emission line of the trial lens L having a distance prescription power. That is, the following formula can be considered.

$$P_{PAL} = P_{SCREEN} \otimes P_{TEST} \quad \text{[Formula 1]}$$

Wherein, $P_{PAL}$ which is the PSF of the blur (second blur component) caused by the progressive addition lens, can be obtained by ray tracing performed to the progressive addition lens in a designing stage. The same thing can be said for $P_{TEST}$ which is the PSF of the blur (first blur component) caused by the trial lens L having a distance prescription power. Therefore, $P_{SCREEN}$ which is the PSF of the blur of the image displayed in the HMD unit, is obtained by Deconvolution calculation. Specifically, $P_{SCREEN}$ which is the PSF of the display blur component can be generated by removing the first blur component from the second blur component.

Figure 4:
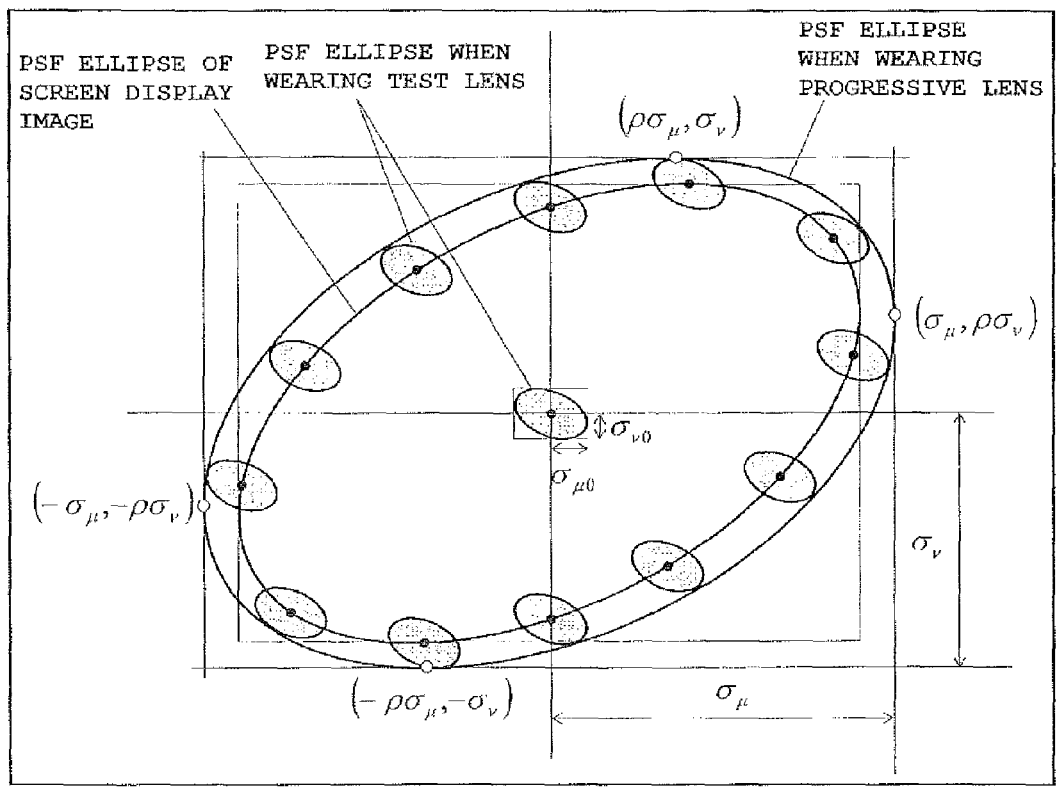
FIG. 4 is a view showing a state of an approximate calculation for calculating a blur according to an embodiment of the present invention.

Since the Deconvolution calculation is significantly complicated, simplified calculation is considered. This method is described using FIG. 4. FIG. 4 is a view showing the approximate calculation state for calculating the blur according to this embodiment.

In this embodiment, an elliptical shape shown in FIG. 4 is a cross-sectional face of a portion obtained by cutting a 3D shape, which is formed on the assumption that a normal distribution curve (curved surface) is formed three-dimensionally in the form of protruding to the Z-axis direction from the XY plane, in a direction parallel to the XY plane with a height of exp $(-\frac{1}{2})=0.6065$ times a peak height of the PSF (normal distribution). A cross-sectionally cut position is the place where exp exponent part is $-\frac{1}{2}$ in the following formula 2. Further, the peak height of the PSF is the place where the exp exponent part is 0.

In the formula, for example the PSF ($P_{PAL}$) when wearing the progressive addition lens can be represented by the following formula.

$$PSF(\mu, v) = \frac{1}{2\pi\sigma_\mu\sigma_v\sqrt{1-\rho^2}}\exp\left(-\frac{1}{2(1-\rho^2)}\left(\frac{\mu^2}{\sigma_\mu^2} - 2\rho\frac{\mu v}{\sigma_\mu\sigma_v} + \frac{v^2}{\sigma_v^2}\right)\right) \quad \text{[Formula 2]}$$

Figure 5:
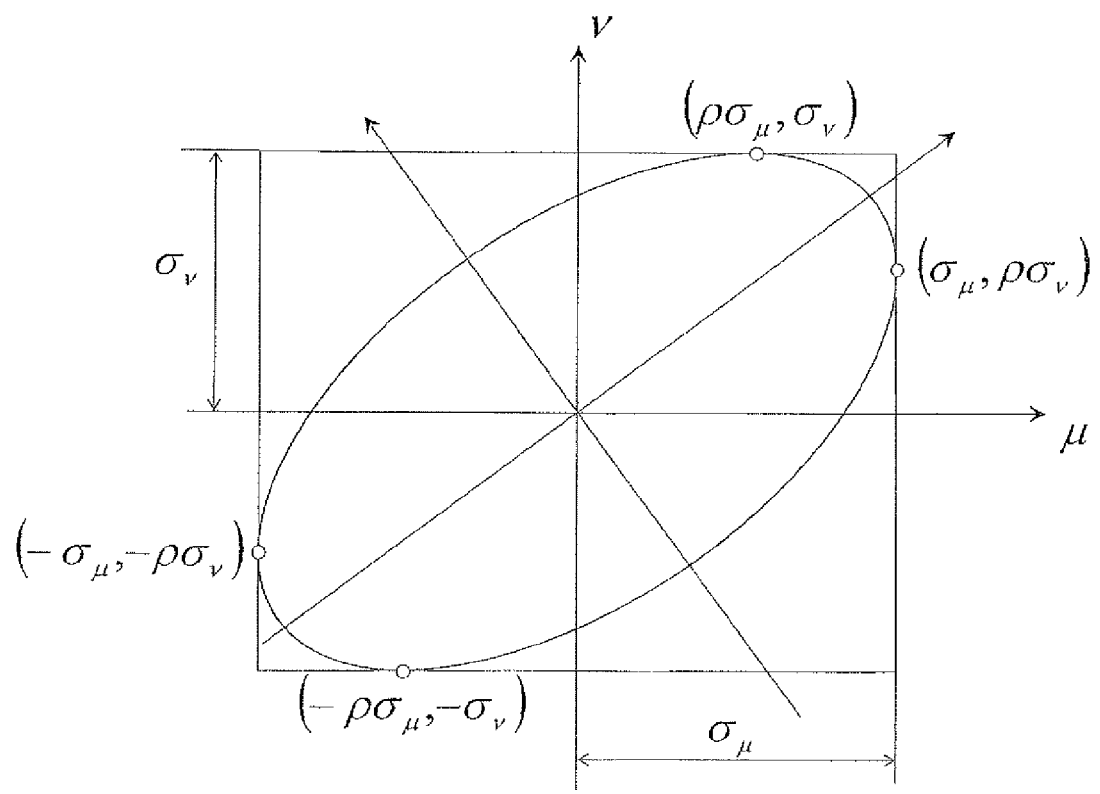
FIG. 5 is a view describing a parameter used for the approximate calculation for calculating the blur according to an embodiment of the present invention.

In the above formula, the ellipse parameters are $\rho$, $\sigma\mu$, the $\sigma v$. FIG. 5 shows the meaning of each parameter.

FIG. 5 is a view showing the parameters used for the approximate calculation for calculating the blur according to this embodiment. Wherein, $\mu$ indicates an axial direction rotated from a longitudinal direction of an ellipse at a predetermined angle, and $v$ indicates a direction vertical to the direction of $\mu$ and rotated from the longitudinal direction of the ellipse at a predetermined angle. Also, $\sigma\mu$ indicates a length from an intersection (origin) of the $\mu$-axis and $v$-axis to a farthest point (for example, $\sigma_\mu$, $\rho\sigma_v$)) in the $\mu$-axial direction. Similarly, $\sigma v$ indicates a furthest point (for example, ($\rho\sigma_\mu$, $\sigma_v$)) from the intersection (origin) of the $\mu$-axis and the $v$-axis in the $v$-axial direction. $\rho$ is a coefficient with respect to the $\mu$-axis coordinate or the $v$-axis coordinate at the abovementioned farthest point, and is a parameter corresponding to the abovementioned "predetermined angle".

Similarly, PSF ($P_{TEST}$) when wearing the trial lens L can be represented by using the above-described formula. The ellipse parameters in this case are $\rho 0$, $\sigma\mu 0$, and $\sigma v 0$.

The inventors of the present invention considers as follows: an ellipse based on $P_{TEST}$ is arranged on an outermost side of the ellipse based on $P_{PAL}$, and the ellipse based on $P_{PAL}$ is reduced to a center position of the ellipse based on $P_{TEST}$ from the outermost side of the ellipse based on $P_{PAL}$, and this is an approximate result of a Deconvolution result of the PSFs (that is, $P_{SCREEN}$ which is the PSF of the display blur component). Based on the above consideration, $\rho'$, $\sigma\mu'$, $\sigma v'$ which are the parameters of the ellipse based on $P_{SCREEN}$ displayed in the screen, can be approximated as follows.

$\rho' = \rho$ $\sigma_\mu' = \sigma_\mu - \sigma_{\mu 0}$ wherein $\sigma_\mu' = 0$ when satisfying $\sigma_\mu < \sigma_{\mu 0}$ $\sigma_v' = \sigma_v - \sigma_{v 0}$ wherein $\sigma_v' = 0$ when satisfying $\sigma_v < \sigma_{v 0}$ There is also a case that $\sigma\mu'$ or $\sigma v'$ calculated in the above-described formula is 0. As the case that $\sigma\mu'$ or $\sigma v'$ is 0, the following case can be considered: the ellipse of $P_{TEST}$ which is the PSF of the blur (first blur component) caused by the trial lens L having a distance prescription power, is larger than the ellipse of $P_{PAL}$ which is the PSF of the blur (second blur component) caused by the progressive addition lens. Such a case means that the blur caused by the trial lens L is large than the blur caused by the progressive addition lens. As a result, it is not necessarily required to carry out Deconvolution calculation, if the approximate calculation can be used, and it is sufficient to take the first blur component into consideration, and there is no necessity for blurring the CG image based on the second blur component. Even in this case, the second blur component is also taken into consideration in such a way that the second blur component is compared with the first blur component. Therefore, there is no change in generating the display blur component based on the first blur component, and the second blur component.

As described above, the PSF ellipse (display blur component) of a screen display image can be relatively easily obtained.

(S5 Display Blur Component Adding Step)

As described above, the display blur component which is the blur caused by only the progressive component of the progressive addition lens to be simulated, is added to the CG image having observation scene data.

(S6 Display Image Output Step)

In the display image output step (S6), a simulation image is generated from the original image by carrying out convolution of the PSF of the pixels.

Note that a detailed technique or structure, etc., of the image processing performed in the display blur component adding step (S5) and the display image output step (S6) may be performed by utilizing the publicly-known technique (see U.S. Pat. No. 3,342,423 and International Publication No. 2010/044383), and therefore explanation thereof is omitted here.

<4. Effect of this Embodiment>

According to this embodiment, the following effect can be exhibited.

First, the view through a plurality of lenses is not employed as a simulation result, by preparing the observation image S not influenced by the trial lens L. Therefore, it becomes possible to reduce the difference between the view when using the simulation device 1 of this embodiment, and the view through one finished progressive addition lens.

Also, unlike the method described in patent document 2, it becomes possible to perform simulation without requiring the spectacle optical system worn by the wearer himself/herself. As a result, even if the optical data of the spectacle optical system worn by the wearer is not possessed by the spectacle shop, on-sight simulation can be performed by the spectacle shop. Then, the simulation result can be provided to the wearer without depending on the progressive addition lens worn by the wearer himself/herself.

Also since the trial lens L is a non-progressive addition lens, the spectacle shop can easily prepare the trial lens L. Further, even in a case of the progressive addition lens based on an individual design, which is a lens of a type designed so as to suit a spectacle wearing condition or a lifestyle of an individual wearer, the progressive component is included in the observation scene data, and therefore even if the progressive addition lens is not especially prepared as an object, the observation image S suited to the desire of an individual wearer can be generated by CG image processing. Therefore, there is no necessity for preparing a plurality of kinds of progressive addition lenses as the trial lens L for confirming the view.

As described in the technique of patent document 2, which is a conventional art, if the image added with blur is created in consideration of all of the spherical power, astigmatic power, and addition power (progressive component), etc., from the first, a calculation amount becomes enormous. That is, in the conventional simulation, calculation must be carried out in the state of many variables (spherical power, astigmatic power, and addition power (progressive component), etc.) when the image is created. However, according to this embodiment, blurring is calculated in consideration of the addition power (progressive component) only in such a manner that the addition is varied under constant distance power. In contrast, the blurring is calculated in consideration of an element other than the progressive component. Thus, the blurring can be calculated by reducing the variables, so that the calculation amount and a required time can be reduced.

Since the blur component is generated by dividing it into the progressive component and a parameter regarding the non-progressive component, it becomes easy to pursuit the cause for the blurring when viewing the image by the wearer, whether the blurring is caused by the image (progressive cause) or the blurring is caused by the trial lens L (non-progressive cause). When it becomes easy to pursuit the cause, the clerk of the spectacle shop can easily find an optimal condition of reducing the blur for the wearer, such as changing the trial lens L, or changing the setting of the image.

The progressive component included in the progressive addition lens significantly depends on the wearer. Therefore, it is extremely troublesome to prepare each lens reflecting the progressive component. Therefore, in this embodiment, the blurring caused by the progressive component, is shared by an image so that data processing can be applied thereto. On the other hand, there is a necessity for having the experience of a view when actually wearing the spectacle, and the wearer must use the spectacle optical system as described in the technique of patent document 2, if no processing such as simulation is attempted. Therefore, the view corresponding to the non-progressive component (spherical power and astigmatic power) is shared by the trial lens L. The lens having the non-progressive component is high versatility, and can sufficiently respond to the desire of a variety of wearers by manufacturing a specific lens so as to be available in the spectacle shop. The concept that the view corresponding to the non-progressive component is shared by the trial lens L and the view corresponding to the progressive component is shared by the image, can be generated on the premise of using the trial lens L. By having the abovementioned structure based on this concept, the view when viewing the outer visual field through the progressive addition lens, can be experienced by the wearer in an order stage of the spectacle lens.

As described above, the simulation device 1 and the simulation system can be provided, which are capable of reducing the difference between the view when having the experience of a view using the trial lens L, and the view when actually wearing the progressive addition lens.

Embodiment 2

The blur component is mainly discussed in the above embodiment. On the other hand, in order to obtain a further precise simulation result, it is further preferable that the distortion component is also reflected on the simulation result.

Figure 8:
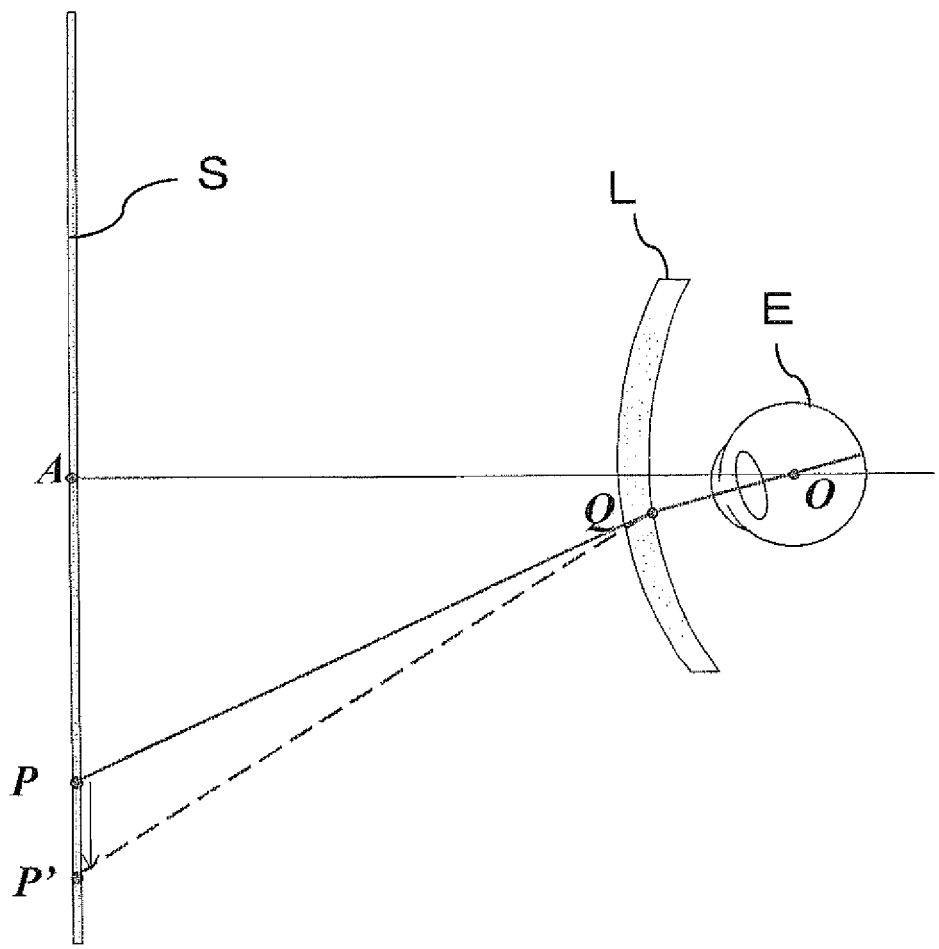
FIG. 8 is a view showing a method of correcting a distortion according to another embodiment of the present invention.

As shown in FIG. 8, the "distortion" is generated when the position of an observation object is appeared to be deviated by an action of a refractive power of the lens. Similarly to the "blur", when viewing a predetermined distance away object, distortion is sometimes generated when wearing one finished progressive addition lens, even when a plurality of trial lenses L are used which have theoretically a specific refractive power in total. That is, it is found by the inventors of the present invention, that the "distortion" is a great factor of the difference of a view, in addition to the "blur".

In addition to removing or adding the blur component, an embodiment of removing or adding a distortion component, will be described hereafter using FIG. 6 to FIG. 8. Specifically, explanation is given for an embodiment of further adding the following each unit, in addition to the structure of [Embodiment 1]. Note that the technique similar to [Embodiment 1] or a publicly-known technique may be used, if not specified otherwise.

<1. Unit for the Distortion Component>
(First Distortion Component Generating Unit 31')

Figure 6:
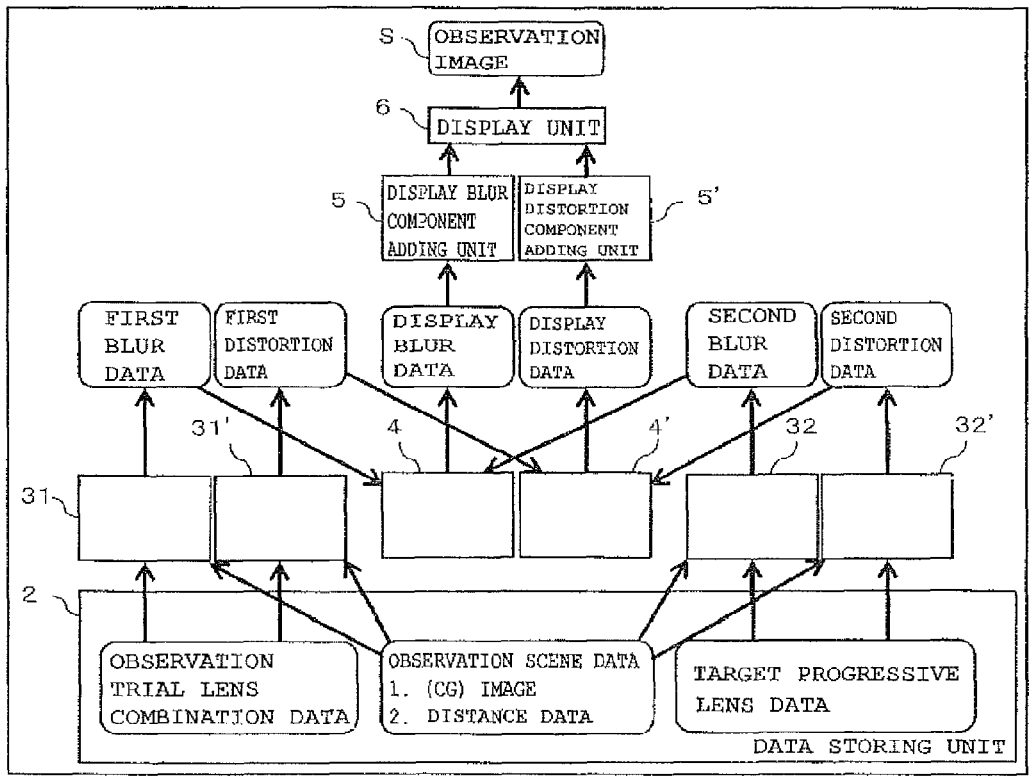
FIG. 6 is a block diagram showing an example of a function configuration of a simulation device according to another embodiment of the present invention.

As shown in FIG. 6, a first distortion component generating unit 31' is the unit having a similar structure as the first blur component generating unit 31. The first distortion component generating unit 31' has a function of retrieving the observation scene data, and the data regarding the trial lens L from the data storing unit 2, and generating the first distortion component based on the distance data included in the observation scene data and the parameter regarding the non-progressive component shared by the trial lens L. The first distortion component is generated due to the non-progressive component shared by the trial lens L, and is converted to the first distortion data.

(Second Distortion Component Generating Unit 32')

A second distortion component generating unit 32' is the unit having a similar structure as the second blur component generating unit 32. The second distortion component generating unit 32' has a function of retrieving the observation scene data and the data regarding the progressive addition lens to be simulated from the data storing unit 2, and generating the second distortion component based on the distance data included in the observation scene data and the parameter regarding the progressive component included in the progressive addition lens. The second distortion component is generated due to the progressive component shared by the image, and is converted to second distortion data.

(Display Distortion Component Generating Unit 4')

A display distortion component generating unit 4' is the unit having a similar structure as the display blur component generating unit 4. The display distortion component generating unit 4' has a function of retrieving first distortion data from the first distortion component generating unit 31', and retrieving second distortion data from the second distortion component generating unit 32', and generating a display distortion component based on the first distortion data and the second distortion data. The display distortion component is influenced by both of the non-progressive component shared by the trial lens L and the progressive component shared by the image, and is converted to display distortion data. Here, the influence of the distortion generated due to the progressive component shared by the progressive addition lens, is given to the CG image. Simultaneously, the influence of the distortion shared by the trial lens L is removed from the CG image.

(Display Distortion Component Adding Unit 5')

A display distortion component adding unit 5' is the unit having a similar structure as the display blur component adding unit 5. The display distortion component adding unit 5' has a function of retrieving display distortion data from the display distortion component generating unit 4', and giving the display distortion data to the CG image.

<2. Procedure of the Simulation Processing Regarding the Distortion Component>

Next, in consideration of the distortion component, explanation is given for an execution procedure of the simulation processing performed so that a trial lens wearer can have a virtual experience of a wearing state of the progressive addition lens.

Figure 7:
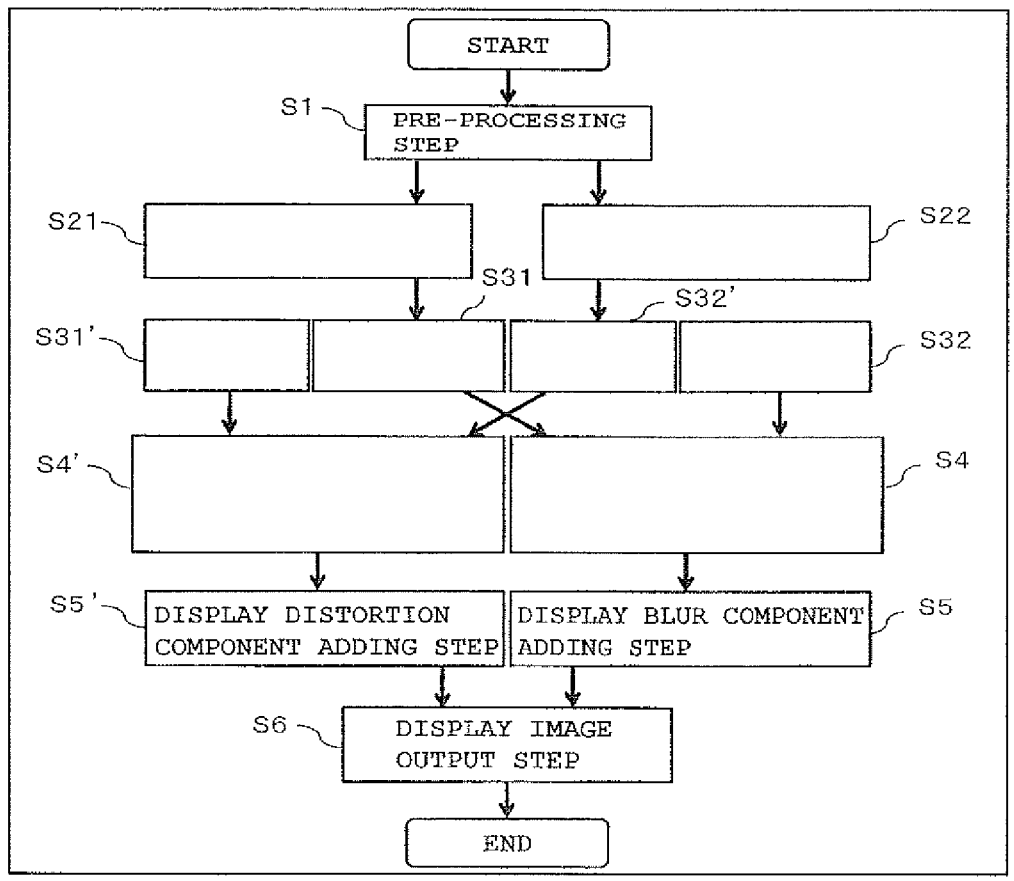
FIG. 7 is a flowchart showing an example of an execution procedure of a simulation processing performed by the simulation device according to another embodiment.

FIG. 7 is a flowchart showing an example of the execution procedure of the simulation processing performed by the simulation device 1 of this embodiment. In this flowchart, the first distortion component generating step (S31') and the second distortion component generating step (S32') are provided in parallel to the first blur component generating step (S31) and the second blur component generating step (S32). Also, the display distortion component generating step (S4') and the display distortion component adding step (S5') are provided, corresponding to the display blur component generating step (S4) and the display blur component adding step (S5) of adding the display blur component to the CG image.

Note that the pre-processing step (S1), the observation trial lens combination acquiring step (S21), and the target progressive lens data acquiring step (S22) are the steps in common with the steps regarding the blur component. Also, the final display image output step (S6) is also the step in common. These steps are descried as shown in the abovementioned embodiment, and therefore the explanation thereof is omitted.

(S31' First Distortion Component Generating Step)

In the first distortion component generating step (S31'), the first distortion component generating unit 31' specifies a generation mode of the distortion of the image generated when the wearer views the outer visual field through the trial lens L. First, a mechanism of generating the distortion will be described using FIG. 8.

FIG. 8 is a view showing a method of correcting the distortion. "A" is the point where a visual ray of an infinite distance vision crosses a screen (observation image S) of the HMD unit. If the wearer wears the finished progressive addition lens provided to the wearer, light beam incident on the progressive addition lens from an observation target corresponding to light beam QO emitted to eyeball E, is indicated by PQ that starts from point P on the screen of the HMD unit. However, actually, the wearer wears the trial lens L having a distance prescription power. Therefore, if no processing is applied, the light beam incident on the progressive addition lens from the observation target, is P'Q starting from point P' on the screen. Accordingly, in order to reproduce the view when wearing the trial lens L having a distance prescription power and wearing a single progressive lens on a provisional frame, the pixel at point P is moved to point P' in all visual directions QO. By this method, the distortion can be corrected. In addition, a direction cosine of the incident light beam PQ when wearing the finished progressive addition lens provided to the wearer, and a direction cosine of the incident light beam P'Q when wearing the trial lens L having a distance prescription power, can be obtained by ray tracing or other publicly-known method.

(S32' Second Distortion Component Generating Step)

Here, the second distortion component is generated. However, unlike the conventional art, the distortion caused by the trial lens L must be removed from the observation image S. In other words, the distortion generated due to only the progressive component included in the progressive addition lens to be simulated, is required to be reproduced in the observation image S.

Regarding the generation of the second distortion component, a method similar to the method of the first distortion component generating step (S31') may be used.

(S4' Display Distortion Component Generating Step)

Here, the display distortion component is generated in consideration of both of the first distortion component and the second distortion component. As a specific method, a method similar to the method of the display distortion component generating step (S4) may be used.

(S5' Display Distortion Component Adding Step)

As described above, the display distortion component which is the distortion generated due to only the progressive component included in the progressive addition lens to be simulated, is added to the CG image having the observation scene data. As a specific method, a method similar to the method of the display distortion component adding step (S5) may be used.

Finally, in the display image output step (S6), the observation image S is prepared after removing the influence of the trial lens L (non-progressive addition lens), not only for the blur component but also for the distortion component. By preparing the observation image S after removing the influence of the trial lens L, the difference between the view when using the simulation device 1 of this embodiment, and the view through one finished progressive addition lens, can be further reduced.

Embodiment 3

In this embodiment, a network form (simulation system) and a programmed form of the structure of the simulation device 1 of [Embodiment 1] will be described.

First, the data storing unit 2 is not necessarily required to be included in the simulation device 1 installed in the spectacle shop. For example, it is also acceptable that data is stored in a different location which is connected by a network server. Then, in the observation trial lens combination acquiring step (S21) and the target progressive lens data acquiring step (S22), the non-progressive component and the progressive component may be obtained from this server as needed.

Also, the first blur component generating unit 31 is not necessarily required to be included in the simulation device 1 installed in the spectacle shop. For example, it is also acceptable that the first blur component may be generated in a different location which is connected by a network server, or the first blur component may be generated by a computer device installed in a manufacturing maker of the progressive addition lens. In addition, the structure that the server plays a role, may be employed for the second blur component generating unit 32, the display blur component generating unit 4, the display blur component adding unit 5, and further employed for each unit related to the distortion component.

In addition, a series of steps described in the above-described embodiment, can be executed as a software processing by a computer, using hardware resources of the computer composed of a combination of CPU (Central Processing Unit), RAM (Random Access Memory), ROM (Read Only Memory), and HDD (Hard disk drive), etc. That is, the function (means) for executing the procedure of the simulation described in this embodiment can be realized by previously installing a software program on HDD, etc., of the computer for performing the abovementioned series of steps, and causing the CPU, etc., of the computer to execute the software program. In this case, the software program may be provided to the computer via a communication line or may be stored in a computer readable memory medium and provided, prior to being installed on HDD, etc.

Embodiment 4

In addition, modified examples other than the above-described embodiment will be described.

(Order of the First Blur Component Generating Step S31 and the Second Blur Component Generating Step S32)

The first blur component generating step S31 and the second blur component generating step S32, may be performed in either order. Further, the abovementioned each step may be performed by a different device via a network in terms of hardware. The same thing can be said for the order of the step regarding the distortion component and a new blur component adding step in which the blur is generated due to the HMD unit. The abovementioned embodiment shows a case that the first blur component generated by the first blur component generating unit, is removed from the second bur component generated by the second blur component generating unit. However, the other case is also acceptable. It is sufficient to add the second blur component or remove the first blur component in some way.

(Left and Right Eyes)

In the above embodiments, at least the display blur component generating unit 4 and the display distortion component generating unit 4' are preferably the units corresponding to the left eye and the right eye individually. Thus, almost no difference can be felt by the wearer, between the view by simulation and the actual view.

(HMD Unit)

In the above embodiments, explanation is given for a case that HMD unit is provided as the display unit 6. Meanwhile, it is also possible to employ a method of screening the observation image S on the screen.

Note that when the HMD unit is provided as the display unit 6, the difference between the view by simulation and the actual view, is sometimes generated, due to an optical system of the HMD unit. The method of the above embodiments can be used for correcting such a difference. More specifically, it is also acceptable that a third blur component generating unit is further provided for generating a third blur component, and the third blur component (third blur data) generated by the third blur component generating unit is removed from the second blur component in the display blur component generating unit 4. In addition, the third blur component generating unit may be provided in parallel to the first blur component generating unit 31 and the second blur component generating unit 32, similarly to each unit related to the blur component described in [Embodiment 2]. In the procedure of the simulation processing as well, the third blur component generating step may be separately provided.

(Observation Scene Data)

The observation scene data of this embodiment is the data in which distance data is added to the CG image. Of course, it is acceptable that the CG image is previously prepared, and the processing of adding distance data may be applied to the CG image. On the other hand, when obtaining the observation scene data, a depth image sensor may be used. If the HMD unit is employed as the display unit 6, not only an image displayer but also an imaging camera and a depth image sensor are incorporated in the casing of the HMD unit.

The imaging camera and the depth image sensor are preferably provided individually corresponding to each one of the left and right eyes of the wearer. However, even when the imaging camera is provided individually corresponding to each one of the left and right eyes of the wearer, it can be considered that one depth image sensor is shared by left and right eyes, if the depth image sensor has a function of correcting depth detection result by the depth image sensor, for left and right eyes.

Further, the depth image sensor capable of handling a moving image similarly to the imaging camera is preferable, and the depth image sensor capable of handling a moving image of a high frame rate is more referable, because it can respond to a smooth video.

The depth image sensor acquires a depth image at the same angle as an imaging result obtained by an imaging camera. The "same angle" used here, includes not only a case that the "angle" exactly matches with each other but also a case that alignment is taken so that the angle is identical, although it is not completely identical.

The depth image sensor is not necessarily required to be a separate body from the imaging camera.

That is, the depth image sensor may be configured integrally with the imaging camera by using a camera device capable of simultaneously acquiring a general two-dimensional RGB image and a depth image having distance information for example.

Supplementary description of the present invention will be described below.

[Supplementary Description 1]

There is provided a simulation method, for having an experience of a view by a wearer when an outer visual field is observed through a progressive addition lens, by observing an observation image through a trial lens, wherein the trial lens is a non-progressive addition lens having a non-progressive component of the progressive addition lens, and shares a role of a view corresponding to the non-progressive component of the progressive addition lens, and the observation image shares a role of a view corresponding to a progressive component of the progressive addition lens, the method including:

a first blur component generating step of generating a first blur component based on distance data included in observation scene data in which the distance data is added to a computer graphics image, and a parameter regarding the non-progressive component of the trial lens;

a second blur component generating step of generating a second blur component based on the distance data included in the observation scene data, and a parameter regarding the progressive component of the progressive addition lens;

a display blur component generating step of generating a display blur component based on the first blur component and the second blur component;

a display blur component adding step of adding the display blur component to the observation scene data; and a display step of displaying an observation image obtained by the display blur component generating step and the display blur component adding step, to a wearer wearing the trial lens.

[Supplementary Description 2]

There is provided a simulation program, for having an experience of a view by a wearer when an outer visual field is observed through a progressive addition lens, by observing an observation image through a trial lens, wherein the trial lens is a non-progressive addition lens having a non-progressive component of the progressive addition lens, and shares a role of a view corresponding to the non-progressive component of the progressive addition lens, and the observation image shares a role of a view corresponding to a progressive component of the progressive addition lens, wherein the program is configured to cause a computer to function as:

a first blur component generating unit of generating a first blur component based on distance data included in observation scene data in which the distance data is added to a computer graphics image, and a parameter regarding the non-progressive component of the trial lens;

a second blur component generating unit of generating a second blur component based on the distance data included in the observation scene data, and a parameter regarding the progressive component of the progressive addition lens;

a display blur component generating unit of generating a display blur component based on the first blur component and the second blur component;

a display blur component adding unit of adding the display blur component to the observation scene data; and a display unit of displaying an observation image obtained by the display blur component adding step, to a wearer wearing the trial lens.

DESCRIPTION OF SIGNS AND NUMERALS

1 Simulation device
2 Data storing unit
31 First blur component generating unit
32 Second blur component generating unit
31' First distortion component generating unit
32' Second distortion component generating unit
4 Display blur component generating unit
4' Display distortion component generating unit
5 Display blur component adding unit
5' Display distortion component adding unit
6 Display unit
L Trial lens
S Observation image
E Eyeball

The invention claimed is:

1. A simulation device for having an experience of a view by a wearer when an outer visual field is observed through a progressive addition lens, by observing an observation image through a set of trial lenses, wherein a trial lens is a non-progressive addition lens having a non-progressive component of the progressive addition lens, and shares a role for a view corresponding to a non-progressive component of the progressive addition lens, and the observation image shares a role for a view corresponding to a progressive component of the progressive addition lens, the simulation device comprising:

a first blur component generating unit configured to generate a first blur component based on distance data included in observation scene data in which the distance data is added to a computer graphics image, and parameters regarding the non-progressive component shared by the trial lens;

a second blur component generating unit configured to generate a second blur component based on distance data included in the observation scene data and parameters regarding the progressive component included in the progressive addition lens;

a display blur component generating unit configured to generate a display blur component, based on the first blur component and the second blur component;

a display blur component adding unit configured to convolute the display blur component into the observation scene data; and a display unit configured to display an observation image obtained by the display blur component adding unit, to a wearer wearing the trial lens.

2. The simulation device according to claim 1, wherein the display blur component is the component in which the first blur component is removed from the second blur component.

3. The simulation device according to claim 2, further comprising:

a first distortion component generating unit configured to generate a first distortion component based on the distance data included in the observation scene data and parameters regarding a non-progressive component included in the trial lens;

a second distortion component generating unit configured to generate a second distortion component, based on distance data included in the observation scene data and parameters regarding a progressive component included in the progressive addition lens;

a display distortion component generating unit configured to generate a display distortion component, based on the first distortion component and the second distortion component; and a display distortion component adding unit configured to practice the display distortion component into the observation scene data, wherein an observation image obtained by the display distortion component adding unit, is displayed by the display unit, to a wearer wearing the trial lens.

4. The simulation device according to claim 3, wherein at least the display blur component adding unit and the display distortion component adding unit respond to each of a left eye and a right eye individually.

5. The simulation device according to claim 4, wherein the display unit is assembled into a casing that can be mounted on a head section of a wearer.

6. The simulation device according to claim 5, comprising:
a third blur component generating unit configured to generate a third blur component, based on distance information between the observation image displayed in the casing and a wearer wherein in the display blur component adding unit, the third blur component generated by the third blur component generating unit is removed from the observation scene data.

7. A simulation system for having an experience of a view by a wearer when an outer visual field is observed through a progressive addition lens, by observing an observation image through a trial lens, wherein the trial lens is a non-progressive addition lens having a non-progressive component of the progressive addition lens, and shares a role for a view corresponding to a non-progressive component of the progressive addition lens, and the observation image shares a role for a view corresponding to a progressive component of the progressive addition lens, the simulation system including:
a first blur component generating unit configured to generate a first blur component based on distance data included in observation scene data in which the distance data is added to a computer graphics image, and a parameter regarding the non-progressive component included in the trial lens;

a second blur component generating unit configured to generate a second blur component based on the distance data included in the observation scene data and a parameter regarding a progressive component included in the progressive addition lens;

a display blur component generating unit configured to generate a display blur component, based on the first blur component and the second blur component;

a display blur component adding unit configured to add the display blur component to the observation scene data; and a display unit configured to display an observation image obtained by the display blur component adding unit, to a wearer wearing the trial lens.

8. A simulation method for having an experience of a view by a wearer when an outer visual field is observed through a progressive addition lens, by observing an observation image through a trial lens, wherein the trial lens is a non-progressive addition lens having a non-progressive component of the progressive addition lens and shares a role for a view corresponding to a non-progressive component of the progressive addition lens, and the observation image shares a role for a view corresponding to a progressive component of the progressive addition lens, the simulation method comprising:
generating a first blur component based on distance data included in observation scene data in which the distance data is added to a computer graphics image, and a parameter regarding the non-progressive component included in the trial lens;

generating a second blur component based on distance data included in the observation scene data and a parameter regarding a progressive component included in the progressive addition lens;

generating a display blur component, based on the first blur component and the second blur component;

adding the display blur component to the observation scene data; and displaying an observation image obtained by the display blur component generating unit and the display blur component adding unit, to a wearer wearing the trial lens.

9. A simulation program for having an experience of a view by a wearer when an outer visual field is observed through a progressive addition lens, by observing an observation image through a trial lens, wherein the trial lens is a non-progressive addition lens having a non-progressive component of the progressive addition lens and shares a role for a view corresponding to a non-progressive component of the progressive addition lens, and the observation image shares a role for a view corresponding to a progressive component of the progressive addition lens, the simulation program configured to cause a computer to function as:
a first blur component generating unit configured to generate a first blur component based on distance data included in observation scene data in which the distance data is added to a computer graphics image, and a parameter regarding the non-progressive component included in the trial lens;

a second blur component generating unit configured to generate a second blur component based on distance data included in the observation scene data and a parameter regarding a progressive component included in the progressive addition lens;

a display blur component generating unit configured to generate a display blur component, based on the first blur component and the second blur component;

a display blur component adding unit configured to add the display blur component to the observation scene data; and a display unit configured to display an observation image obtained by the display blur component adding unit, to a wearer wearing the trial lens.

* * * * *